US012594230B2

(12) United States Patent
Kim et al.

(10) Patent No.: US 12,594,230 B2
(45) Date of Patent: Apr. 7, 2026

(54) SPHINGOLIPID CONTAINING SALICYLIC ACID DERIVATIVE AND COMPOSITION COMPRISING SAME

(71) Applicant: Croda Korea Ltd, Iksan-si (KR)

(72) Inventors: Ara Kim, Yongin-si (KR); Kwanhyoung Lee, Yongin-si (KR); Daebang Seo, Yongin-si (KR)

(73) Assignee: Croda Korea Ltd, Iksan-si (KR)

( * ) Notice: Subject to any disclaimer, the term of this patent is extended or adjusted under 35 U.S.C. 154(b) by 457 days.

(21) Appl. No.: 18/004,553

(22) PCT Filed: Dec. 28, 2020

(86) PCT No.: PCT/KR2020/019241
§ 371 (c)(1),
(2) Date: Jan. 6, 2023

(87) PCT Pub. No.: WO2022/010055
PCT Pub. Date: Jan. 13, 2022

(65) Prior Publication Data

US 2024/0252414 A1 Aug. 1, 2024

(30) Foreign Application Priority Data

Jul. 9, 2020 (KR) ........................ 10-2020-0084867

(51) Int. Cl.
*A61K 8/68* (2006.01)
*A61Q 5/00* (2006.01)
*C07C 235/60* (2006.01)

(52) U.S. Cl.
CPC .................. *A61K 8/68* (2013.01); *A61Q 5/00* (2013.01); *C07C 235/60* (2013.01); *A61K 2800/33* (2013.01)

(58) Field of Classification Search
None
See application file for complete search history.

(56) References Cited

U.S. PATENT DOCUMENTS

2005/0245464 A1* 11/2005 Yedgar .................... A61P 29/00 514/59
2007/0003509 A1 1/2007 Farwick et al.
2008/0249073 A1 10/2008 Farwick et al.
2009/0010968 A1 1/2009 Allart et al.
2014/0170092 A1* 6/2014 Farwick .................. A61K 8/41 424/59

FOREIGN PATENT DOCUMENTS

KR 10-2000-0070718 A 11/2000
KR 10-2013-0004448 A 1/2013
KR 10-2019-0114864 A 10/2019
WO 2019/173584 A1 9/2019

OTHER PUBLICATIONS

National Center for Biotechnology Information. "PubChem Compound Summary for CID 2244, Aspirin" PubChem, https://pubchem.ncbi.nlm.nih.gov/compound/Aspirin. Accessed Oct. 28, 2025.*
Office Action dated Feb. 15, 2023, issued in Korean Application No. 10-2020-0084867.
S. Naumann et al., "Penetration Studies of an Extremely Lipophilic Active Model Substance from an Oil-in-Water Emulsion: Influence of the Lipophilicity of the Formulation in Human Skin—Part 2", Skin Pharmacology and Physiology, 2014, pp. 97-105, vol. 27.
International Search Report for PCT/KR2020/019241 dated Apr. 23, 2021.
Office Action (The Third Office Action) issued Jul. 24, 2024, by the State Intellectual Property Office of People's Republic of China in corresponding Chinese Patent Application No. 202080103861.6 and an English translation. (13 pages).

* cited by examiner

*Primary Examiner* — Nicole P Babson
(74) *Attorney, Agent, or Firm* — Buchanan Ingersoll & Rooney PC

(57) ABSTRACT

A composition for skin application and uses thereof are disclosed. The composition includes a sphingolipid containing a salicylic acid derivative as an active ingredient. The composition including a sphingolipid containing a salicylic acid derivative may exhibit, when applied to the scalp, an effect of alleviating scalp erythema, an effect of increasing the amount of moisture in the scalp, an effect of inhibiting scalp sebum secretion, an effect of inhibiting scalp itchiness, and the like.

13 Claims, 5 Drawing Sheets

SPHINGOLIPID CONTAINING SALICYLIC ACID DERIVATIVE AND COMPOSITION COMPRISING SAME

CROSS REFERENCE TO RELATED APPLICATIONS

This application is a National Stage of International Application No. PCT/KR2020/019241 filed Dec. 28, 2020, claiming priority based on Korean Patent Application No. 10-2020-0084867 filed Jul. 9, 2020.

TECHNICAL FIELD

The present invention relates to a novel sphingolipid containing a salicylic acid derivative and to a composition containing the same and capable of stabilizing sensitive, irritable, and reactive scalp and effectively alleviating itching, fever, inflammation, and the like of scalp.

BACKGROUND ART

Skin, as a barrier organ of the human body, is subjected to external influences to a particular extent and irritated by many intrinsic factors, such as genetic predisposition, and extrinsic factors, such as actions of UV light or allergy-inducing substances. Therefore, various compositions for providing continuous care to the skin while alleviating such skin irritation have been developed.

Currently, approximately 10 to 20% of the total domestic population has symptoms of atopic dermatitis. Conventionally, atopic dermatitis was developed intensively in children, but the incidence thereof decreased after age five and thus many people showed disappeared or mitigated symptoms in adults. However, with rapid industrialization, living environments have been cleaned and the probability of exposure to external irritants becomes lowered, which leads weakening immune systems, and thus the number of atopic dermatitis patients increases by 10% or more every year. This atopic dermatitis is a chronic inflammatory skin disease that causes persistent itching and acute or chronic eczema lesions of the skin, and may be accompanied by asthma, allergic rhinitis, and the like, in addition to skin lesions. In atopic dermatitis, a large amount of water evaporated from the skin surface causes drying in the skin and a higher acidity of the skin compared with the skin of normal persons. In addition, a decrease in the overall lipid content of the stratum corneum reduces antibacterial activity and weakens the barrier function, thereby decreasing defense against external stimuli, causing inflammatory responses by external stimuli and the resultant itching.

Itching has two clinical meanings: one is hypersensitive itching that one feels itching even by a very weak stimulus that normally causes no itching; and the other is itching like a stinging pain, which is caused by an external stimulus irrelevant to itching. The onset of these two types of itching is caused by various external factors, and in order to relieve the itching thus caused, one scratches the skin, which results in again itching, thereby forming a circular loop, resulting in a vicious cycle with increasing inflammatory disease along with itching. Itching is intricately connected with an inflammatory response in the skin, and the blocking of itching inhibition may be regarded as a look-ahead problem for the treatment of various diseases caused thereby.

Skin delivers about 65 to 70% of water in the human body, that is, various physiologically active substances necessary for the human body and plays an important role in controlling the evaporation, to the outside of the body, of this moisture, which helps keep the skin soft and moist. The stratum corneum of the epidermis contains about 10 to 20% of moisture, and is present in the outermost layer of the human body, thereby suppressing the evaporation of water to the outside of the body and blocking excessive penetration of substances from the outside. Due to several causes, such as artificial temperature control of air conditioning/heating according to environment changes or lifestyle changes, various types of stresses caused in social life and skin stresses by environmental pollution, frequent face-washing resulting from make-up habits, and natural skin aging with age, the water in the stratum corneum decreases to cause dry skin, rough skin surfaces, and lusterless and dark skin, and thus the need for skin moisturizers is increasing.

Currently, steroid preparations, topical immunosuppressants, and anti-histamine preparations for improving inflammatory responses, along with moisturizers that keep the water in the skin surface, have been used as inflammatory skin disease medicines or atopic skin disease medicines, but the long-term use of the preparations causes problems, such as thinning skin, skin discoloration, osteoporosis, arteriosclerosis, possibility of carcinogenesis, and deterioration of symptoms due to tolerance. Steroids, antihistamines, immunosuppressants, and the like are administered topically and systemically to treat itching, but such medicines cause drowsiness, lowered immunity, and problems in terms of safety on the skin and stability in the formulation of compositions, and thus the use thereof is restricted. Hence, there is a steady need to develop raw materials or pharmaceuticals retaining anti-inflammatory and anti-itching efficacy while showing no such side effects.

Itching is a common symptom of atopy, psoriasis, contact dermatitis, or sensitive skin disease, and especially, the sensitive skin disease is accompanied by sensory-unpleasant itching after use of cosmetics or detergents, such as soaps and shampoos, in spite of the absence of any clinical or histological symptoms related to skin lesions. In addition, one of the typical diseases that cause most severe itching is a scalp disease, and the scalp disease may be itching caused by the proliferation of dandruff bacteria, dry scalp, residues left after use of soaps or shampoos, or hair loss. In most cases, scalp itching is caused by rapid dryness of the skin due to skin itching or the like, and preventing scalp dryness and relieving itching is needed above all. However, steroid preparations or preparations containing substances for enhancing antibacterial and anti-inflammatory functions of the steroid preparations are merely developed in the conventional art, and these preparations could not be a fundamental solution to scalp itching, and most of the developed preparations were shampoos and the like and thus contain surfactants to raise concerns about severe side effects when applied to the skin for a long period of time.

Ceramides are a specific group of sphingolipids including sphingosine, phytosphingosine, or dihydrosphingosine (sphinganine) as a base (sphingoid base) for an amide bond with a fatty acid. Ceramides are a most important component that accounts for 50 to 60% of lipid components constituting the stratum corneum, the outermost layer, in contact with outside air and play a main role in keeping the water of the skin to moisturize the skin.

Therefore, the present inventors have attempted to develop pseudoceramide compounds and apply the compounds to compositions for scalp improvement.

PRIOR ART DOCUMENT (Patent Document) Korean Patent No. 10-1458108

DISCLOSURE OF INVENTION

Technical Problem

An aspect of the present invention is to provide a composition for application to the skin to be capable of stabilizing sensitive, irritable, and reactive scalp and effectively alleviating itching, fever, inflammation, and the like of the scalp.

Another aspect of the present invention is to provide a cosmetic composition for use in scalp improvement.

Still another aspect of the present invention is to provide a cosmetic composition for use in anti-aging.

Still another aspect of the present invention is to provide a hair cosmetic composition.

Still another aspect of the present invention is to provide an externally-applied composition for itching relief.

Solution to Problem

In accordance with an aspect of the present invention, there is provided a sphingolipid having a salicylic acid derivative and represented by Chemical Formula 1 below

[Chemical Formula 1]

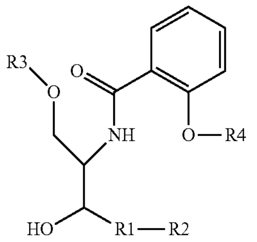

wherein,

R1 is $CH_2—CH_2$, CH═CH, or $C(H)OH—CH_2$;

R2 is a straight or branched chain alkyl, alkenyl, or alkynyl group of 12 to 20 carbon atoms;

R3 is H or a straight or branched chain alkyl or alkenyl group of 1 to 10 carbon atoms;

R4 is H or C═OR5; and

R5 is any one selected from the group consisting of $CH_3$, $CH_2CH_3$, or $CH_2CH_2CH_3$.

In accordance with another aspect of the present invention, there is provided a composition for application to the skin, the composition containing, as an active ingredient, the sphingolipid or a pharmaceutically acceptable salt or solvate thereof.

In accordance with still another aspect of the present invention, there is provided a cosmetic composition containing the composition for application to the skin.

In accordance with still another aspect of the present invention, there is provided a hair cosmetic composition containing the sphingolipid.

In accordance with still another aspect of the present invention, there is provided an externally applied composition for relieving itching containing the sphingolipid.

Advantageous Effects of Invention

The compositions containing a sphingolipid having a salicylic acid derivative of the present invention can exhibit a scalp erythema relieving effect, a scalp water content increasing effect, a scalp sebum secretion inhibiting effect, a scalp itching inhibiting effect, and the like when applied to the scalp. Therefore, the compositions of the present invention can be a fundamental solution to scalp diseases by replacement with conventional steroid preparations, topical immunosuppressants, anti-histamine preparations, and the like.

Furthermore, the compositions of the present invention can exhibit an anti-aging effect.

The compositions of the present invention cause no side effects due to the absence of surfactants even when applied to the skin for a long period of time, and thus can be applied to cosmetic products and medicinal products.

BEST MODE FOR CARRYING OUT THE INVENTION

Hereinafter, the present invention will be described in detail.

The present inventors, while making an intensive endeavor to develop a substance capable of stabilizing sensitive, irritable, and reactive scalp and effectively alleviating itching, fever, inflammation, and the like of the scalp, developed a composition containing, as an active ingredient, a novel sphingolipid having a salicylic acid derivative and applied the composition to the scalp, and as a result the present inventors verified that the composition exhibited a scalp erythema relieving effect, a scalp water content increasing effect, a scalp sebum secretion inhibiting effect, a scalp itching inhibiting effect, and the like, and thereby completed the present invention.

As used herein, the term "sphingolipid" refers to a generic term of lipids having a long chain sphingoid base and encompasses sphingoglycolipids, sphingophospholipids, or ceramides.

Sphingolipids have, as a common structure, a ceramide structure having irregular chain lengths in which a long chain fatty acid is bound to an amino group of a sphingoid via an acid-amide bond.

<Sphingolipid Containing salicylic acid Derivative>

An embodiment of the present invention relates to a sphingolipid having a salicylic acid derivative and represented by Chemical Formula 1 below.

[Chemical Formula 1]

wherein,

R1 is $CH_2—CH_2$, CH═CH, or $C(H)OH—CH_2$;

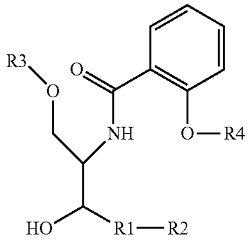

R2 is a straight or branched chain alkyl, alkenyl, or alkynyl group of 12 to 20 carbon atoms;

R3 is H or a straight or branched chain alkyl or alkenyl group of 1 to 10 carbon atoms;

R4 is H or C═OR5; and

R5 is any one selected from the group consisting of $CH_3$, $CH_2CH_3$, or $CH_2CH_2CH_3$.

R2 may be preferably a straight chain alkyl group of 12 to 15 carbon atoms.

R3 may be preferably H or a hydrocarbon of 2 to 8 carbon atoms.

Specifically, the compound of Chemical Formula 1 is a compound including, as a sphingoid base, sphingosine, dihydrosphingosine, or phytosphingosine, binding with acetylsalicylic acid via an imide bond.

The sphingolipid used in the present invention contains a salicylic acid derivative.

Herein, the "sphingolipid having a salicylic acid and represented by Chemical Formula 1" is also referred to as "pseudoceramide compound represented by Chemical Formula 1".

Figure 2:
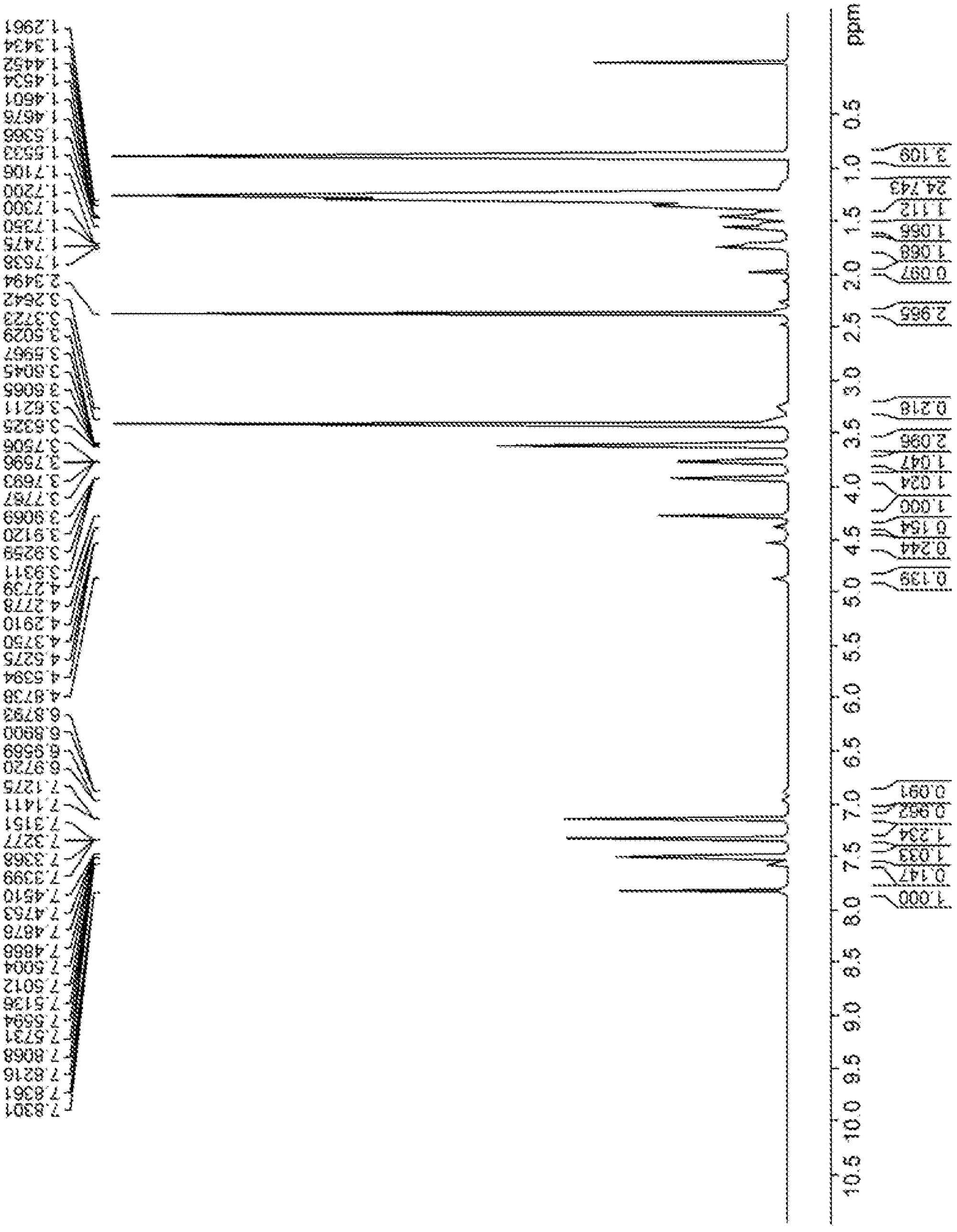
FIG. 2 shows nuclear magnetic resonance spectroscopy analysis results of a sphingolipid containing acetylated salicylic acid of Example 1.

When the chemical shift (δ) of methyl hydrogen in the reference substance tetramethylsilane is defined as 0 ppm in the spectrum obtained by nuclear magnetic resonance spectroscopy, the sphingolipid has peak data of 6.5 to 8.5 ppm (see FIG. 2).

The sphingolipid may have a purity of 50% or more, preferably 70% or more, and more preferably 90% or more.

The present invention provides a salt, preferably a pharmaceutically acceptable salt, of the pseudoceramide compound represented by Chemical Formula 1.

Herein, the term "pharmaceutically acceptable salt" refers to a salt suitable for use in contact with the tissues of human beings and lower animals without excessive toxicity, irritation, allergic response, and the like within the scope of sound medical judgment. The pharmaceutically acceptable salt has been well known in the art and, for example, is detailed in literature (S. M. Berge et al., J. Pharmaceutical Sciences, 66, 1, 1977). The salts may be prepared in the same reaction system during the final isolation and purification of the compound of the present invention or may be prepared by separate reaction with an inorganic or organic base. Preferred examples of the base addition salt form may include: ammonium salts; alkali salts and earth alkaline metal salts, for example, salts of lithium, sodium, potassium, magnesium, and calcium; salts with organic bases, for example, salts of primary, secondary and tertiary aliphatic and aromatic amines, such as methylamine, ethylamine, propylamine, isopropylamine, four types of butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline, benzathine, N-methyl-D-glucamine, 2-amino-2-(hydroxymethyl)-1,3-propanediol, and hydrabamine; and salts with amino acids, such as arginine and lysine.

In addition, the present invention may contain a hydrate or solvate of the pseudoceramide compound represented by Chemical Formula 1, or derivative compounds thereof. Of the solvates, solvents are not particularly limited and may include all the conventional solvents known in the art.

The pseudoceramide compound represented by Chemical Formula 1 may be prepared by isolation from a natural product, purification, and then predetermined treatment (acylation) or may be prepared by chemical synthesis methods known in the art.

In an embodiment, the pseudoceramide compound represented by Chemical Formula 1 may be obtained by isolating a fatty acid oil derived from a natural plant, for example, a natural plant (e.g., sea buckthorn, palm, sunflower, rapeseed, canola, olive, coconut, soybean, etc.) or an animal (e.g., horse, cattle, sheep, bee, fish, crustacean, human, etc.), followed by purification, and then separating a ceramide from the fatty acid oil, and then subjecting the separated ceramide to acylation by a conventional method known in the art.

In addition, a desired pseudoceramide may be further subjected to a process, as fractionation, for isolation and/or purification, and as a fraction solvent used herein, the extraction solvent may be used without limitation. The pseudoceramide compound may be purified by employing a purification method known in the art. As an example of the purification method, isolation and purification may be performed by concentration gradient chromatography combined with additional purification including reverse phase partition chromatography, normal phase adsorption chromatography, ion exchange chromatography, size exclusion chromatography, or a combination of one or more thereof. For the chromatography methods, column chromatography, high performance liquid chromatography (HPLC), and the like, which use the filling of various types of resins, such as silica gel and active alumina, may be used alone or in combination. However, the extraction and isolation purification of compounds is not essentially limited to the above methods.

The above-described pseudoceramide compound represented by Chemical Formula 1, an isomer thereof, or a pharmaceutically acceptable salt or solvate thereof is easily dissolved and dispersed in various oils at room temperature while having an excellent moisturizing effect inherent to existing thus the ceramides, and pseudoceramide compound can be advantageously used in all the fields to which ceramides are applied.

<Composition for Application to Skin>

Another embodiment of the present invention is directed to a composition for application to skin, the composition containing a sphingolipid having a salicylic acid derivative and represented by Chemical Formula 1 or a pharmaceutically acceptable salt or solvate thereof as an active ingredient.

As used herein, the term "active ingredient" refers to an ingredient that can alone show desired activity alone or together with a carrier that per se is not active.

Herein, the composition for skin application may be formulated to contain a cosmetologically, pharmaceutically, or dermatologically acceptable medium or base. The composition may be provided in the form of any formulation suitable for topical application, for example, a solution, a gel, a solid, an anhydrous product of a paste, an emulsion obtained by dispersing an oil phase in a water phase, a dispersion, a micro-emulsion, a micro-capsule, micro-granules, or an ionic (liposome) or non-ionic vesicular dispersant, or in the form of a cream, a skin, a lotion, a powder, an ointment, a spray, a pack, or a concealer stick. The composition may also be used in the form of a foam or an aerosol composition further containing a compressed propellant, but is not limited thereto. These compositions may be prepared by common methods in the art.

The composition for application to the skin of the present invention containing the above-described pseudoceramide compound can be applied to all of the fields where conventional ceramides are used.

Specifically, the composition may be a composition for application to the skin for use in enhancing anti-inflammation or moisturization, removing sebum, alleviating itching, or preventing hair loss, and more specifically, a pharmaceutical composition, cosmetic composition, and/or quasi-drug composition, for use in the application to the skin. However, the composition of the present invention is not particularly limited thereto.

The content of the sphingolipid may be 0.0001 to 55 wt %, and preferably 0.001 to 10.0 wt %, relative to the total weight of the composition. Less than 0.0001 wt % of the active ingredient may show a slight scalp improving effect, and more than 55 wt % of the active ingredient may degrade the stability of formulations.

The composition for application to the skin according to the present invention may contain the sphingolipid and thus have a pH of 3-9.

The composition for application to the skin according to the present invention may further contain common ingredients known in the art in addition to the above-described ingredient. For example, the composition may contain a ceramide, cholesterol, a fatty acid, a free sphingoid base, a phospholipid, or a mixture thereof. The ceramide, cholesterol, fatty acid, and free sphingoid base are typically main components constituting intercellular lipids, and the phospholipid is a main substance that constitutes cell walls and can effectively prevent the evaporation of water in the skin epidermis and maximize the water retention in the skin through similar structures and compositions to intercellular lipids.

The ceramide is one of the intercellular lipid components constituting the stratum corneum of the skin, accounts for 40% or more of the skin lipids, and functions to maintain and restore the skin barrier, and thus it is necessary to maintain or supplement the ceramides in maintaining skin elasticity. Nine types of ceramides constitute the skin. Non-limiting examples of usable ceramides may be ceramide 1 (EOS), ceramide 2 (NS), ceramide 3 (NP), ceramide 4 (EOH), ceramide 5 (AS), ceramide 6 (NH), ceramide 7 (AP), ceramide 8 (AH), ceramide 9 (EOP), or a mixture thereof. The content of the ceramide is not particularly limited, and may be appropriately adjusted within a content range known in the art.

The composition for application to the skin may further contain, as a free sphingoid base, at least one of phytosphingosine, sphingosine, and sphinganine. The free sphingoid bases, which are intermediates in the biosynthetic pathways of ceramides, may serve to supplement deficient ceramide components or enable skin cells to directly synthesize ceramides when applied to the skin. The contents of the above-described ingredients are not particularly limited, and may be appropriately adjusted within content ranges known in the art.

In the present invention, the composition for application to the skin may be a cosmetic composition or pharmaceutical composition that can be applied to the skin, but is not particularly limited thereto.

The composition for application to the skin of the present invention may be a composition containing no surfactant. Therefore, the composition of the present invention causes no side effects even when applied to the skin for a long period of time, and thus can be suitable for cosmetic products or medicinal products.

<Cosmetic Composition>

Another embodiment of the present invention is directed to a cosmetic composition containing the above-described composition for application to the skin. In an embodiment, the cosmetic composition contains the above-described pseudoceramide compound represented by Chemical Formula 1 or a cosmetologically acceptable salt or solvate thereof as an active ingredient.

The cosmetic composition is preferably used for scalp improvement, preferably at least one selected from the group consisting of alleviating scalp inflammation, relieving scalp itching, improving scalp moisturizing, soothing scalp, inhibiting dandruff bacterial growth, and preventing hair loss, but is not particularly limited thereto.

The content of the compound of Chemical Formula 1 as an active ingredient in the cosmetic composition according to the present invention is not particularly limited, and may be appropriately adjusted according to the type and purpose of use, skin condition, type and severity of symptoms, and the like.

The cosmetic composition of the present invention may contain ingredients commonly used in cosmetic compositions, in addition to the above-described pseudoceramide compound represented by Chemical Formula 1 or a pharmaceutically acceptable salt or solvate thereof. For example, the cosmetic composition of the present invention may contain common adjuvants known in the art, such as stabilizers, solubilizers, vitamins, pigments, and flavors, carriers, and purified water, without limitation. The cosmetic composition of the present invention may further contain water-soluble vitamins, oil-soluble vitamins, high-molecular peptides, high-molecular polysaccharides, sphingolipids, natural extracts, waxes, oils, detergents, surfactants, colorants, and flavoring agents, which are commonly used in cosmetic compositions, within the scope of not impairing the purpose of the present invention.

The cosmetic composition of the present invention may be prepared in any formulation that is commonly prepared in the art, and the formulation may be appropriately selected according to the purpose. For example, the cosmetic composition of the present invention may take the formulation of a solution, an emulsion, or a viscous mixture, and as a specific example, the cosmetic composition may be formulated into at least one selected from a cream, an essence, a lotion, a skin, a gel, an ointment, an oil, and a tonic. However, the cosmetic composition is not limited thereto.

Particularly, the pseudoceramide compound according to the present invention is oil-soluble and highly miscible at room temperature without the use of an emulsifier, and thus can be usefully applied to hair care products and/or scalp care products.

A method for preparing the cosmetic composition according to the present invention is not particularly limited, and a method known in the art can be applied without limitation. Hereinafter, the preparation method is not limited only by the following preparation methods, wherein respective process steps may be modified or selectively mixed as needed.

An example of the preparation method may include steps of: (i) preparing a lipid phase by dissolving, in an oil, a pseudoceramide compound represented by Chemical Formula 1, cholesterol, a fatty acid, and a phospholipid; (ii) preparing an aqueous phase by mixing water with a mixture of a free sphingoid base and an organic acid; and (iii) mixing the lipid phase in step (i) and the aqueous phase in step (ii) under heating, followed by addition of a preservative.

As the cholesterol used in the present invention, any common substance that is known in the art may be used.

As the phospholipid, any common component known in the art may be used without limitation, and non-limiting examples thereof may include hydrogenated lecithin, hydrogenated phosphatidylcholine, phospholipids, hydrogenated lysophosphatidylcholine, hydrogenated lysolecithin, hydroxylated lecithin, unsaturated lecithin, or a mixture of one or more thereof.

As the fatty acid, any common component known in the art may be used, and for example, a straight chain saturated fatty acid of 12 to 30 carbon atoms, preferably 18 to 26 carbon atoms, may be used. Non-limiting examples of the fatty acid include lauric acid, myristic acid, palmitic acid, stearic acid, oleic acid, branched chain lauric acid, branched chain myristic acid, branched chain palmitic acid, branched chain stearic acid, branched chain oleic acid, or a mixture of one or more thereof.

In step (i), the lipid phase containing the pseudoceramide, cholesterol, fatty acid, and phospholipid is preferably added to oil and then dissolved under heating at 80 to 85° C. As the oil, any common component known in the art may be used, and examples thereof may include silicone oils, hydrocarbon oils, higher fatty acid oils, ester oils, glyceride oils, lanolin oils, plant oils, or mixtures thereof.

The cosmetic composition according to the present invention may be prepared by mixing the lipid part, dissolved under heating, with the aqueous phase under heating and then optionally adding the preservative.

The content ratio (mixing ratio) of the lipid phase and the aqueous phase is not particularly limited, and may be appropriately adjusted within a range known in the art.

The temperature of the aqueous phase may be 75 to 80° C. As the aqueous part, a polyhydric alcohol, water, or a mixture thereof may be used, and preferably, the aqueous phase may be a mixture of a polyhydric alcohol and water.

According to an embodiment of the present invention, the cosmetic composition may be used for anti-aging.

According to an embodiment of the present invention, the cosmetic composition may be a hair cosmetic composition containing a sphingolipid having a salicylic acid derivative and represented by Chemical Formula 1.

<Externally Applied Composition>

Another embodiment of the present invention is directed to an externally applied composition for relieving itching containing a sphingolipid having the above-described salicylic acid derivative and represented by Chemical Formula 1. As a specific example, the externally applied composition contains as an active ingredient the above-described pseudoceramide compound represented by Chemical Formula 1 or a pharmaceutically acceptable salt or solvate thereof.

The externally applied composition according to the present invention may further contain adjuvants, such as pharmaceutically suitable and physiologically acceptable carriers, excipients, and diluents, in addition to the above-described pseudoceramide compound represented by Chemical Formula 1 or a pharmaceutically acceptable salt or solvate thereof. Representative examples of the pharmaceutically acceptable carriers, excipients, or diluents may include lactose, dextrose, sucrose, sorbitol, mannitol, xylitol, maltitol, starch, gelatin, glycerin, acacia gum, alginate, calcium phosphate, calcium carbonate, calcium silicate, cellulose, methyl cellulose, microcrystalline cellulose, polyvinyl pyrrolidone, water, methyl hydroxybenzoate, propyl hydroxybenzoate, talc, magnesium stearate, mineral oils, propylene glycol, polyethylene glycol, plant oils, injectable esters, Witepsol, Macrogol, Tween 61, cocoa butter, laurin butter, and the like. For example, the pharmaceutical composition may be made into a preparation by using an excipient, a binder, a disintegrant, a lubricant, a solubilizer, a suspending agent, a preservative, or an extender.

The externally applied composition may be formulated in any dosage form known in the art, such as a cream, a gel, a patch, a spray, an ointment, a plaster, a lotion, a liniment, a paste, or a cataplasm.

The usage of the pseudoceramide compound of Chemical Formula 1 as an active ingredient in the externally applied composition according to the present invention may be adjusted according to the type and purpose of use, patient condition, type and severity of symptoms. External administration may be performed once or in divided doses per day. However, external administration is not particularly limited thereto.

MODE FOR CARRYING OUT THE INVENTION

Hereinafter, the present invention will be described in detail with reference to examples and comparative examples. These examples are provided only for the purpose of illustrating the present invention in more detail, and it would be apparent to a person skilled in the art that the scope of the present invention is not limited by these examples.

Example 1: Preparation of Acetylsalicylated Sphingolipid

Acetylated salicylic acid was dissolved in ethyl acetate, and then tosyl chloride and 4-dimethylaminopyridine (DMAP) were added thereto. After reaction at 60° C. for 0.5 hours, phytosphingosine (R1=(C(H)OH—$CH_2$), R2=($C_{13}H_{27}$), R3=(H)) was added. After the addition of phytosphingosine, reaction was conducted for 2 hours, and then the reaction solution was cooled to 10° C. and filtered to obtain a white filtrate.

Figure 1:
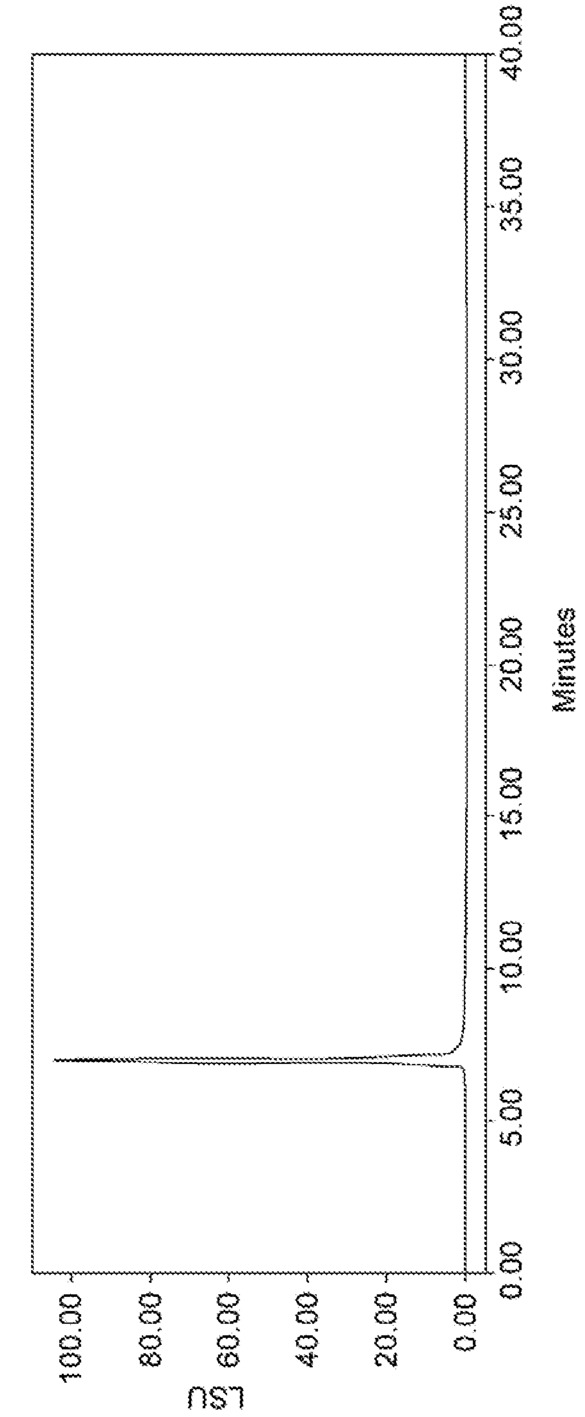
FIG. 1 shows high performance liquid chromatography analysis results of a sphingolipid containing acetylated salicylic acid of Example 1.

The obtained white filtrate was dried, and then subjected to silica thin layer chromatography (development conditions: chloroform+methanol+formic acid=190:15:1, color development with 10% sulfuric acid), liquid chromatography, and NMR analysis to confirm a sphingolipid containing acetylated salicylic acid and having an area value of 99%, that is, acetylsalicylated sphingolipid (see FIGS. 1 and 2).

Example 2: Preparation of Hair Tonic

The acetylsalicylated sphingolipid prepared in Example 1 was used to prepare a hair tonic of Example 2 according to the composition shown in Table 1 below.

TABLE 1

| Ingredient name | INCI name | Content (%) |
|---|---|---|
| Purified water | Purified water | Remainder |
| Citric Acid | Citric Acid | 0.02 |
| Na-Citrate | Sodium Citrate | 0.03 |
| Aminocoat | Betaine | 1.00 |

TABLE 1-continued

| Ingredient name | INCI name | Content (%) |
|---|---|---|
| Niacin B | Niacinamide | 1.00 |
| D-Panthenol | Panthenol | 0.20 |
| Acetylsalicylated sphingolipid of Example 1 | | 0.01 |
| HCO-40 | PEG-40 Hydrogenated Castor oil | 1.00 |
| 1,3-BG | Butylene glycol | 10.00 |
| EtOH | Alcohol Denat. | 25.00 |

Test Example 1: Scalp Erythema Relieving Effect

The hair tonic formulation of the present invention was evaluated for a scalp erythema relieving effect as follows.

Fifteen adults with scalp erythema were recruited to use the hair tonic prepared in Example 2 twice a day for 4 weeks, and then were measured for scalp erythema by analyzing a* values through a spectrophotometer (CM2600d), thereby evaluating a scalp erythema relieving effect by sample application. Specifically, before use of the product (0 week) and on 2 and 4 weeks after use of the product, sites of test were subjected to three times of repeated measurement, and the average measurement values before and after were compared and the results are shown in FIG. 3.

Figure 3:
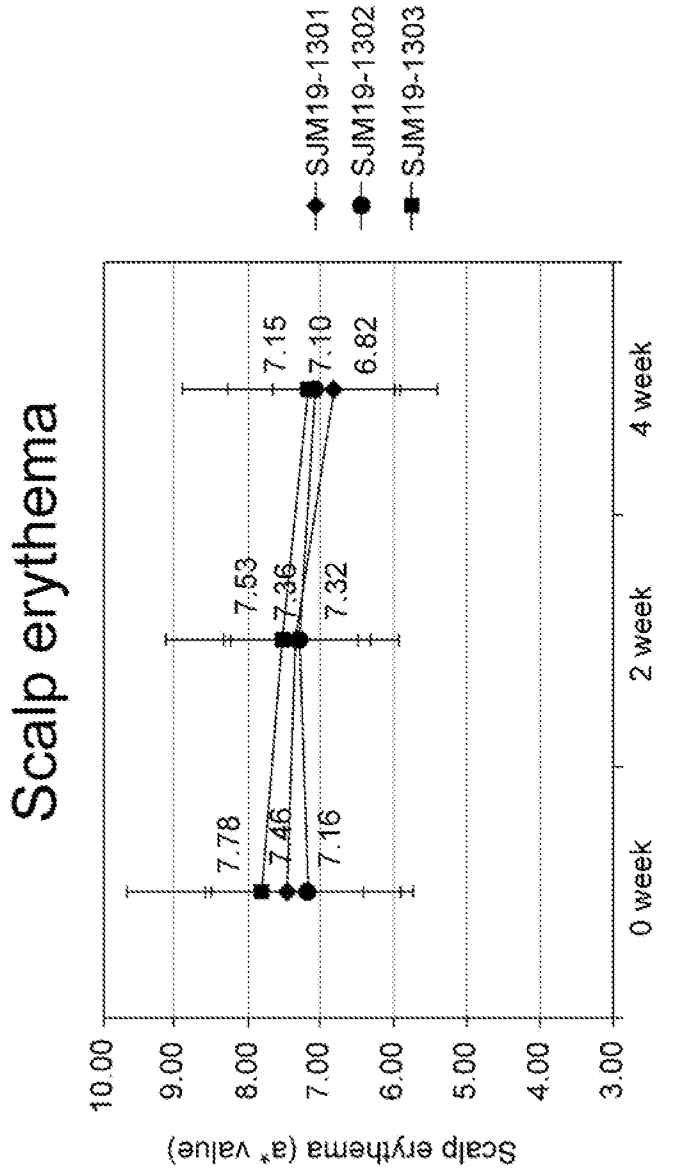
FIG. 3 shows scalp erythema measurement results when a hair tonic formulation containing a sphingolipid having acetylated salicylic acid of Example 2 was clinically applied.

As can be seen from FIG. 3, as a result of using the hair tonic of Example 2, erythema was reduced after 4 weeks relapsed. It was therefore confirmed that the cosmetic composition according to the present invention had a scalp erythema relieving effect.

Test Example 2: Scalp Water Content Increasing Effect

The hair tonic formulation of the present invention was evaluated for a scalp water content increasing effect.

Specifically, fifteen adults were recruited to use the hair tonic prepared in Example 2 twice a day for 4 weeks, and measured for the scalp water content by DermaLab® USB Hydration. Specifically, before use of the product (0 week) and on 2 and 4 weeks after use of the product, sites of test were subjected to three times of repeated measurement, and the average measurement values before and after were compared and the results are shown in FIG. 4.

Figure 4:
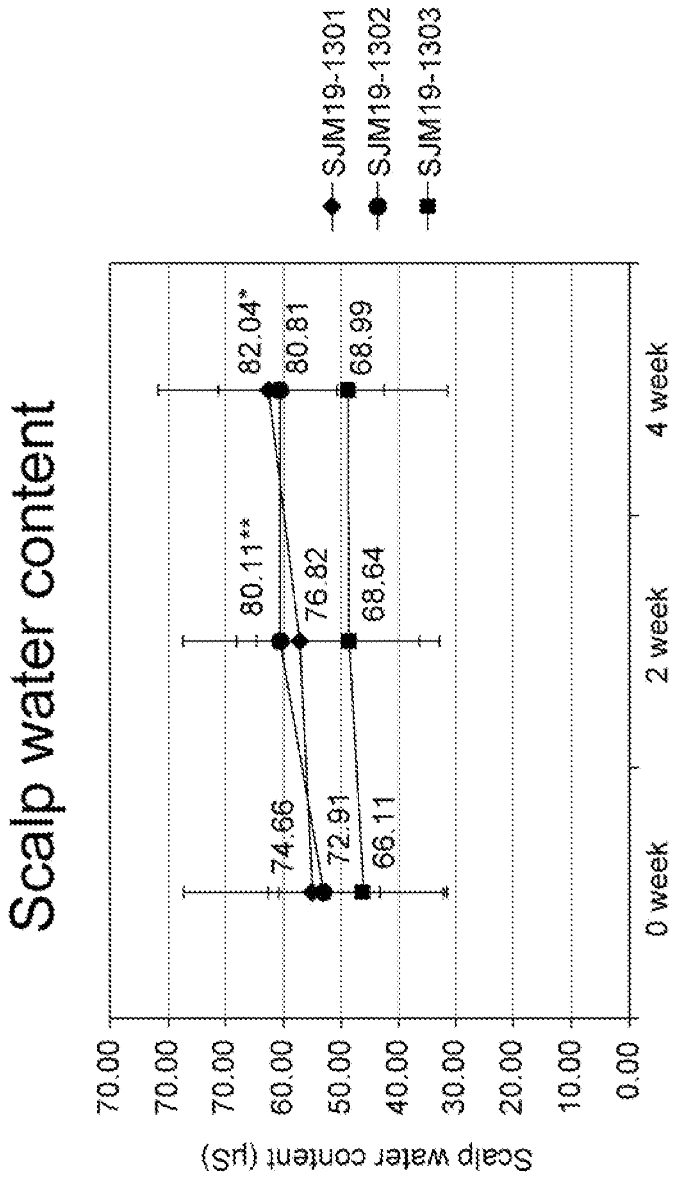
FIG. 4 shows scalp water content measurement results when a formulation containing a sphingolipid having acetylated salicylic acid of Example 2 was clinically applied.

As shown in FIG. 4, as a result of using the hair tonic of Example 2, the water content continuously increased from immediately after use until 4 weeks elapsed. It was therefore confirmed that the cosmetic composition according to the present invention had a scalp water content increasing effect.

Test Example 3: Change in Scalp Sebum Secretion Rate

The hair tonic formulation of the present invention was evaluated for a scalp sebum secretion removing effect as follows.

Fifteen adults were recruited to use the hair tonic prepared in Example 2 twice a day for 4 weeks, and measured for the scalp sebum secretion rate by Skin-o-mat® Sebumeter. Specifically, before use of the product (0 week) and on 2 and 4 weeks after use of the product, sites of test were subjected to three times of repeated measurement, and the average measurement values before and after were compared and the results are shown in FIG. 5.

Figure 5:
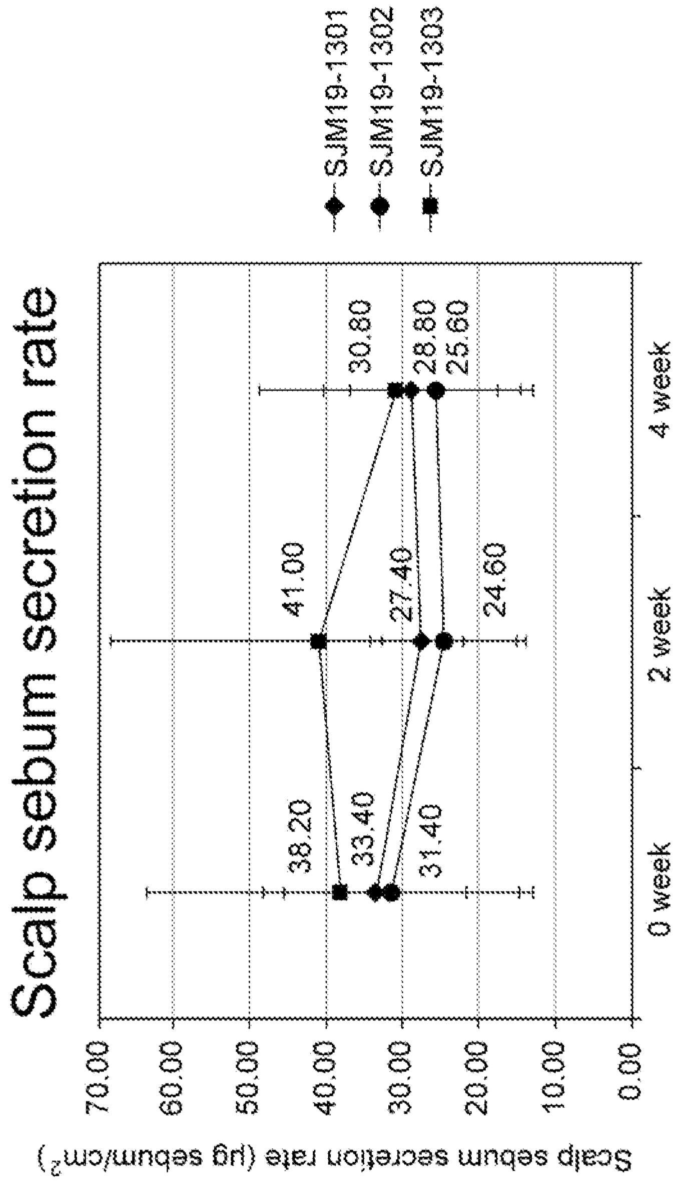
FIG. 5 shows scalp sebum secretion rate measurement results when a formulation containing a sphingolipid having acetylated salicylic acid of Example 2 was clinically applied.

As can be seen from FIG. 5, as a result of using the hair tonic of Example 2, the scalp sebum secretion rate was reduced. It was therefore confirmed that the cosmetic composition according to the present invention had a scalp sebum secretion removing effect.

Test Example 4: Scalp Itching Inhibiting Effect

The hair tonic formulation of the present invention was evaluated for a scalp itching inhibiting effect as follows.

Fifteen adults with scalp itching were recruited to use the hair tonic of Example 2 twice a day for 4 weeks, and measured for a scalp itching inhibiting effect by the following determination method, and the results are shown in Table 2 below.

TABLE 2

| Scalp itching inhibiting effect | Example 2 |
|---|---|
| Excellent | 10 |
| Good | 4 |
| Slight | 1 |
| No | 0 |

As can be seen from Table 2, it was confirmed that the hair tonic of Example 2 had an excellent scalp itching inhibiting effect.

The invention claimed is:

1. A sphingolipid having a salicylic acid derivative and represented by Chemical Formula 1:

[Chemical Formula 1]

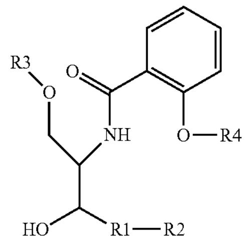

or a pharmaceutically acceptable salt or solvate thereof, wherein:

R1 is C(H)OH—$CH_2$;

R2 is $C_{13}H_{27}$;

R3 is H;

R4 is C═OR5; and

R5 is $CH_3$.

2. A composition for application to the skin, the composition comprising the sphingolipid of claim 1 or a pharmaceutically acceptable salt or solvate thereof.

3. The composition of claim 2, wherein the sphingolipid is present in an amount of 0.0001 to 55 wt % relative to the total weight of the composition.

4. The composition of claim 2, wherein the composition has a pH of 3 to 9.

5. The composition of claim 2, further comprising at least one of phytosphingosine, sphingosine, and sphinganine.

6. The composition of claim 2, further comprising at least one of ceramide 1 (EOS), ceramide 2 (NS), ceramide 3 (NP), ceramide 4 (EOH), ceramide 5 (AS), ceramide 6 (NH), ceramide 7 (AP), ceramide 8 (AH), and ceramide 9 (EOP).

7. The composition of claim 2, wherein the composition comprises no surfactant.

8. The composition of claim 2, wherein the composition is capable of scalp improvement.

9. The composition of claim 8, wherein the scalp improvement is at least one selected from the group consisting of alleviating scalp inflammation, relieving scalp itching, improving scalp moisturizing, soothing scalp, inhibiting dandruff bacterial growth, and preventing hair loss.

10. The composition of claim 2, wherein the composition is formulated into at least one selected from the group consisting of a cream, an essence, a lotion, a toner, a gel, an ointment, an oil, and a tonic.

11. A cosmetic composition comprising the sphingolipid of claim 1 and one or more water-soluble vitamins, oil-soluble vitamins, high-molecular peptides, high-molecular polysaccharides, sphingolipids, natural extracts, waxes, oils, detergents, surfactants, colorants, and flavoring agents.

12. The composition of claim 11, wherein the composition is capable of anti-aging.

13. An externally applied composition capable of relieving itching comprising the sphingolipid of claim 1.

* * * * *